United States Patent [19]

Moghe et al.

[11] Patent Number: 5,635,164

[45] Date of Patent: Jun. 3, 1997

[54] STICK COMPOSITION WITH SODIUM CHLORIDE AND STEARYL ALCOHOL

[75] Inventors: Bhalchandra D. Moghe, Edison; Radhakrishna B. Kasat, Bellemead, both of N.J.

[73] Assignee: The Mennen Company, Morristown, N.J.

[21] Appl. No.: 725,677

[22] Filed: Jul. 3, 1991

[51] Int. Cl.$^6$ ..................................................... A61K 7/32
[52] U.S. Cl. .......................................... 424/65; 424/DIG. 5
[58] Field of Search ............................... 424/DIG. 5, 65

[56] References Cited

U.S. PATENT DOCUMENTS

| | | | |
|---|---|---|---|
| 4,322,400 | 3/1982 | Yuhas | 424/59 |
| 4,331,653 | 5/1982 | Brown et al. | 424/66 |
| 4,382,079 | 5/1983 | Marschner | 424/65 |
| 4,414,200 | 11/1983 | Murphy et al. | 424/66 |
| 4,425,328 | 1/1984 | Nabial | 424/66 |
| 4,504,465 | 3/1985 | Sampson et al. | 424/66 |
| 4,518,582 | 5/1985 | Schamper et al. | 424/66 |
| 4,524,062 | 6/1985 | Laba et al. | 424/66 |
| 4,725,432 | 2/1988 | May | 424/66 |
| 5,010,110 | 4/1991 | Wilmott et al. | 424/68 |

FOREIGN PATENT DOCUMENTS

| | | |
|---|---|---|
| 013390 | 12/1979 | European Pat. Off. . |
| 107330 | 9/1983 | European Pat. Off. . |
| 272919 | 12/1987 | European Pat. Off. . |
| 284765 | 2/1988 | European Pat. Off. . |

OTHER PUBLICATIONS

"Household & Personal Products", vol. 28, No. 7 (Jul. 1991), p. 18.

*Primary Examiner*—Shelley A. Dodson
*Attorney, Agent, or Firm*—Antonelli, Terry, Stout & Kraus, LLP

[57] ABSTRACT

Disclosed is a clear cosmetic stick composition (e.g., a clear deodorant solid stick) having a base of polyhydric alcohol (e.g., propylene glycol) and/or monohydric alcohol (e.g., ethanol), and water, and gelled with sodium salt of saturated fatty acids of $C_{12}$–$C_{22}$, and further including sodium chloride and stearyl alcohol. Inclusion of both sodium chloride and stearyl alcohol reduces crystal formation in the composition, thereby improving clarity and appearance of the composition.

29 Claims, No Drawings

STICK COMPOSITION WITH SODIUM CHLORIDE AND STEARYL ALCOHOL

BACKGROUND OF THE INVENTION

The present invention relates to stick-type cosmetic compositions, in particular, solid stick deodorant compositions. More specifically, the present invention relates to a deodorant composition containing a base of a polyhydric (e.g., propylene glycol) and/or monohydric (e.g., ethanol) alcohol, together with water, gelled with alkali metal salts of saturated fatty acids, having improved clarity and appearance. In particular, the present invention relates to clear deodorant compositions containing propylene glycol and water, as the base, and gelled with sodium salts of saturated fatty acids having a carbon length of 12-22 (that is, sodium salts of relatively long carbon chain length fatty acids), having improved clarity and appearance without crystal formation (that is, wherein the composition does not form crystals over a period of time after formation of the composition).

It has been desired to provide clear cosmetic stick compositions (for example, clear deodorant solid stick compositions) having a composition base of a polyhydric alcohol (e.g., a glycol such as propylene glycol) and/or a monohydric alcohol (e.g., ethanol), together with water, gelled with, e.g., sodium salts of saturated fatty acids, wherein crystal formation after forming of the composition is reduced (thereby to improve clarity of the composition and appearance of the product). This problem of crystal formation, and reduced clarity and appearance of the product, is especially acute where the alkali metal salts (e.g., sodium salts) of saturated fatty acids include those with relatively long carbon chain lengths of the fatty acid (for example, a carbon chain length up to $C_{22}$). Use of such relatively long carbon chain length fatty acids is desired in that they provide a product having a relatively high melting temperature and, correspondingly, relatively greater stability.

U.S. Pat. No. 4,382,079 to Marschner discloses a deodorant cosmetic stick consisting essentially of at least about 0.1–3% and up to about 70% of an alkali metal bicarbonate, and about 0.10% suspending agent, dispersed in a soap-based gel which comprises a major amount of an aqueous or anhydrous polyhydric alcohol or a mixture of a polyhydric alcohol and monohydric alcohol, gelled by a minor amount of an alkali metal salt of a fatty acid containing 14 to 20 carbon atoms. This patent discloses that the sodium or potassium soap-based gel into which the aqueous bicarbonate solution or suspension is incorporated includes a polyhydric alcohol or a mixture of a polyhydric and monohydric alcohol, suitable polyhydric alcohols including glycerin and the lower alkylene glycols of low molecular weight which are liquid at room temperature, such as ethylene glycol, diethylene glycol, butylene glycol and preferably propylene glycol. This patent further discloses that any type of high molecular weight saturated fatty acid may be used as the fatty acid for the alkali metal (e.g., sodium or potassium) salt utilized as the gelling agent, although it is preferred to employ commercial stearic acid which includes essentially a mixture of stearic and palmitic acids ($C_{16}$ and $C_{18}$ acids).

Although disclosing soap-based stick deodorant compositions wherein the gelling agents, of alkali metal salts of saturated fatty acids, utilize fatty acids with a carbon chain length up to 20, this patent does not disclose any crystallization problems occurring, which can effect clarity and appearance of the final product. In fact, this patent is primarily concerned with incorporation of bicarbonate in the stick, and discloses that the transparency of the bicarbonate stick is reduced as the solubility of the bicarbonate in the soap gel is reduced. Moreover, this patent discloses that preferably sodium salts of commercial stearic acid (containing relatively short carbon chain stearic and palmitic acids) are utilized as the gelling agent. Thus, this patent, in particular, does not address the acute problem of crystal formation occurring in sticks based on alcoholic soap gels gelled with, e.g., sodium salts of saturated fatty acids having a relatively long carbon chain length, up to and beyond $C_{22}$.

U.S. Pat. No. 4,322,400 to Yuhas discloses stick-type cosmetic compositions. The compositions contain, as a basic vehicle, a mixture of water and sodium stearate in proportions sufficient to form a self-supporting solid composition which does not readily deform, and yet is not so firm that a hard, waxy composition results which will not leave a deposit of the active ingredient on skin to which the composition is applied. The composition described in this patent further includes (in addition to the active ingredient, water and sodium stearate) water-compatible polyhydroxyl compounds such as glycerin, a glycol or a polyglycol, to modify the physical properties of the composition and impart an improved "feel", and relatively small amounts of sodium chloride. The sodium chloride is added in order to prevent "syneresis" (that is, exuding of water from the solid stick), at temperature extremes of 0°–40° C. or more than 50° C. This patent discloses that the addition of the relatively small amounts of sodium chloride also increases the settling point, as well as the rate of setting, of the water-sodium stearate cosmetic stick base. This patent further discloses that the sodium chloride can be employed in an amount of at least about 0.5 weight %, and preferably at least about 1 weight %, and up to about 5 weight %, based upon the water-sodium stearate vehicle.

U.S. Pat. No. 4,322,400 is primarily concerned with incorporation of sodium chloride into sodium stearate-gelled water-based compositions, and does not further define the gelling agent apart from disclosing use of "sodium stearate". This patent does not disclose crystallization problems, particularly such problems when relatively long carbon chain fatty acids are utilized in the gelling agent, and only discloses that sodium chloride is included to avoid "syneresis" problems and achieve increased settling point and rate of setting (that is, this patent does not disclose incorporating sodium chloride in the cosmetic stick composition to avoid crystallization problems).

U.S. Pat. No. 4,725,432 to May discloses solid stick compositions, based upon waxy materials of long-chain fatty alcohols in combination with volatile silicones, such compositions also containing an alcohol selected from the group consisting of (1) $C_{20}$ alcohols, (2) those alcohols whose chains are longer than $C_{20}$, and (3) mixtures of (1) and (2), at levels of from about 1% to about 3% of the total long-chain fatty alcohols present in the compositions. This patent further discloses that the long-chain fatty alcohols forming the base of the composition are those having melting points of from about 100° F. to about 150° F., these including fatty alcohols containing from about 8 to about 18 carbon atoms in their chains, suitable examples including cetyl alcohol, stearyl alcohol, myristyl alcohol, lauryl alcohol and mixtures thereof.

U.S. Pat. No. 4,725,432 is not a water or alcohol/water-based stick composition gelled with alkali metal salts of saturated fatty acids. Moreover, this patent does not disclose clear compositions; and does not teach the problem of crystal formation in deodorant compositions having a base of alcohol and water gelled with alkali metal salts of saturated fatty acids, or the particularly acute problem of crystal formation occurring when the gelling agent includes relatively long-length carbon chain fatty acids.

As seen in the foregoing, the references do not address the problem of crystal formation, which reduces clarity and appearance of the solid stick composition including a base of alcohol and water, gelled with alkali metal salts of saturated fatty acids; or the particularly acute problem of crystal formation occurring where the saturated fatty acids have a relatively long carbon chain length up to and beyond $C_{22}$. Moreover, the compositions disclosed in these references do not inherently solve this problem. Accordingly, it is still desired to provide a cosmetic stick composition (e.g., a clear deodorant solid stick composition) having a base of polyhydric and/or monohydric alcohol and water, gelled with alkali metal salts of saturated fatty acids, avoiding crystal formation of such composition and its associated reduction of clarity and appearance of the product.

SUMMARY OF THE INVENTION

Accordingly, it is an object of the present invention to provide a cosmetic stick composition (e.g., a deodorant stick composition) having improved clarity and appearance (that is, wherein the clarity and appearance of the product when formed is not reduced over a time period after formation of the composition).

It is a further object of the present invention to provide a clear cosmetic stick composition (e.g., clear deodorant solid stick composition) having reduced crystallization, and a correspondingly improved clarity and appearance of the composition.

It is a still further object of the present invention to provide a clear cosmetic stick composition comprising a base including polyhydric and/or monohydric alcohol, and water, gelled with alkali metal salts of saturated fatty acids, having improved clarity and appearance.

It is a still further object of the present invention to provide a cosmetic stick composition (in particular, a deodorant solid stick composition) having a base including polyhydric and/or monohydric alcohol, and water, gelled with alkali metal salts of saturated fatty acids, such saturated fatty acids being relatively long-length carbon-chain saturated fatty acids, having reduced crystal formation and a correspondingly improved clarity and appearance.

It is a further object of the present invention to provide a clear cosmetic stick composition, having a composition base of propylene glycol and water and gelled with sodium salts of saturated fatty acids (in particular, saturated fatty acids of $C_{12}$–$C_{22}$ carbon chain length), having reduced crystal formation and a correspondingly improved clarity and appearance.

The foregoing objects are achieved by incorporating both sodium chloride and stearyl alcohol in the cosmetic stick composition including a base of polyhydric and/or monohydric alcohol and water, gelled with alkali metal salts of saturated fatty acids.

Accordingly, the composition of the present invention includes, as essential ingredients, polyhydric and/or monohydric alcohol and water, as a base, gelled with alkali metal salts of saturated fatty acids, and further including both sodium chloride and stearyl alcohol.

Of course, other ingredients conventionally known to be incorporated in cosmetic stick compositions (e.g., deodorant solid stick compositions, such as for combatting axillary odors) can also be included in the composition of the present invention. For example, the present invention contemplates incorporation of conventional deodorant active materials (e.g., for combatting axillary odors), including (but not limited to) fragrancing components and bacteriostats, as well as filler materials such as talc, colloidal silica, clays, etc.

Through use of both sodium chloride and stearyl alcohol incorporated in the stick composition, reduced crystal formation, and a resulting improved clarity and appearance, as compared to corresponding stick compositions incorporating either sodium chloride or stearyl alcohol (but not both), and as compared to compositions incorporating neither sodium chloride or stearyl alcohol, is achieved.

The problem of crystal formation in stick compositions comprising a base including polyhydric and/or monohydric alcohol and water, gelled with alkali metal salts of saturated fatty acids, is particularly acute with solid stick compositions gelled with alkali metal (e.g., sodium) salts of fatty acids of $C_{12}$–$C_{22}$ carbon chain length; such problem substantially does not occur where the fatty acids are of $C_{16}$–$C_{18}$ carbon chain length (that is, where maximum carbon chain length is relatively short). However, when the gelling agent utilizes fatty acids of $C_{16}$–$C_{18}$ chain length, the compositions melt at too low a temperature and the formed product is not sufficiently stable. Thus, it is desired to utilize, as the gelling agent, alkali metal salts (e.g., sodium salts) of saturated fatty acids of relatively long carbon chain length (e.g., up to $C_{22}$, including mixtures of salts of $C_{12}$–$C_{22}$ fatty acids).

Accordingly, through use of the present invention, a relatively stable cosmetic stick composition, based on alcohols and gelled with alkali metal salts of relatively long carbon chain length saturated fatty acids, can be achieved, without problems of crystal formation reducing the clarity and appearance of the composition.

Thus, by the present invention, a clear cosmetic solid stick composition (e.g., a clear deodorant solid stick composition), including a base of polyhydric and/or monohydric alcohol and water, gelled with alkali metal salts of saturated fatty acids (in particular, sodium salts of relatively long carbon chain length saturated fatty acids), with reduced crystal formation after forming of the composition, and having corresponding improved clarity and appearance, can be achieved. Through use of the present invention, both the surface quality (that is, less surface crystals) and clarity (delay in formation of crystals internally in the formed product) are improved. Moreover, the overall gel strength is also improved (that is, syneresis is decreased).

DETAILED DESCRIPTION OF THE INVENTION

While the invention will be described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Throughout the present specification, where compositions are described as including or comprising specific components, it is contemplated by the inventors that compositions of the present invention also consist essentially of, or consist of, the recited components. Accordingly, throughout the present disclosure any described composition can consist essentially of, or consist of, the recited components.

The present invention contemplates a cosmetic stick composition (in particular, a clear stick composition, including clear deodorant sticks) including at least one of a polyhydric and/or monohydric alcohol and water, as the base, such base being gelled with alkali metal salts of saturated fatty acids, the composition further including both sodium chloride and stearyl alcohol. The incorporation of both sodium chloride and stearyl alcohol in the composition reduces crystal formation, over the course of time after formation of the composition (e.g., in the final product), thereby improving clarity and appearance of the product.

The polyhydric alcohol utilized according to the present invention can be any of those known for use in forming cosmetic sticks, including (but not limited to) propylene glycol, dipropylene glycol, glycerol and sorbitol. Preferred is propylene glycol. Various polyhydric alcohols used in cosmetic stick compositions (in particular, deodorant stick compositions) are disclosed in U.S. Pat. No. 4,382,079, the contents of which patent are incorporated herein by reference in their entirety.

Additional specific polyhydric alcohols which can be utilized in cosmetic stick compositions are also disclosed in U.S. Pat. No. 4,322,400 (designated as "polyhydroxyl compounds" in this patent), the contents of which patent are incorporated herein by reference in their entirety.

Monohydric alcohols (e.g., ethanol) can also be utilized as part of the base, gelled with the alkali metal salt of the fatty acid, according to the present invention. Generally, various monohydric alcohols, such as ethanol or isopropyl alcohol, have been utilized, as also discussed in U.S. Pat. No. 4,382,079 (the contents of which, in their entirety, have previously been incorporated herein by reference).

The present invention has its greatest effect, in reducing crystal formation, when utilizing alkali metal salts (sodium salts) of saturated fatty acids having carbon chain lengths of $C_{12}$–$C_{22}$ (that is, a distribution of different fatty acids in the gelling agent). A typical distribution of fatty acids for the gelling agent is shown in the following:

| C-Chain Length | % Range (by weight of the total fatty acids) |
|---|---|
| $C_{12}$ Lauric | 0–1 |
| $C_{14}$ Myristic | 4–10 |
| $C_{16}$ Palmitic | 20–30 |
| $C_{18}$ Stearic | 25–42 |
| $C_{20}$ Arachidic | 15–18 |
| $C_{22}$ Behenic | 17–20 |

The objectives of the present invention are achieved incorporating both sodium chloride and stearyl alcohol in the composition. Illustratively, the sodium chloride can be incorporated in the composition in amounts of 0.1 to 3.0% by weight, of the weight of the total composition; and the stearyl alcohol can be incorporated in the composition in an amount of 0.1 to 1.0% by weight, of the total weight of the composition. Preferred ranges for the sodium chloride and stearyl alcohol are, respectively, 0.3 to 0.6% by weight and 0.1 to 0.4% by weight.

Depending on the use of the cosmetic stick composition (for example, as a deodorant solid stick), various additional ingredients can be added to the previously discussed components. When used as a deodorant, the composition can include various materials, illustratively including perfumes, coloring agents, thickeners or viscosity builders, bacteriostats, etc. Various optional ingredients which can be incorporated in the composition, when such composition is utilized as a deodorant solid stick, are described in U.S. Pat. No. 4,382,079, the contents of which have previously been incorporated herein by reference in their entirety.

Attention is also directed to U.S. Pat. No. 4,322,400, the contents of which have already been incorporated herein by reference in their entirety, disclosing various optional ingredients incorporated in the stick composition so as to provide deodorant sticks, perfume sticks, insect repellant sticks, etc.

In the following is set forth specific ranges of various components of the stick composition, when optional components are incorporated so as to provide a deodorant stick. These ranges, shown in the following Table 1, are illustrative and not limiting.

TABLE 1

| Item | % by weight in the composition |
|---|---|
| Propylene Glycol | 50–80 |
| Water | 15–40 |
| Sodium Stearate | 6–9 |
| Perfume | 0.5–2 |
| Triclosan | 0.05–0.4 |
| Sodium Chloride | 0.1–3.0 |
| Stearyl Alcohol | 0.1–1.0 |

The solid stick compositions of the present invention are made in accordance with well-established methods known to those knowledgeable in the art. In particular, attention is directed to U.S. Pat. No. 4,382,079 and U.S. Pat. No. 4,322,400, the contents of each of which have been incorporated herein by reference in their entireties, which each describes techniques of forming the stick composition, as well as, e.g., liquid-filling the composition into a package so as to form a final packaged product.

Of course, the present stick composition can be used (e.g., in a deodorant stick), as conventionally utilized by the consumer.

EXAMPLES

In the following Table 2 are shown six specific deodorant stick compositions, the first five of which fall outside the scope of the present invention (that is, the first five contain either sodium chloride or stearyl alcohol, but not both), and the sixth falls within the scope of the present invention (that is, the sixth contains both sodium chloride and stearyl alcohol).

TABLE 2

| ITEM | 1 | 2 | 3 | 4 | 5 | 6 |
|---|---|---|---|---|---|---|
| Propylene Glycol | 70 | 70 | 70.25 | 70 | 70 | 70 |
| Water | 22.1 | 19.7 | 21.1 | 21.45 | 21.25 | 20.95 |
| Sodium Stearate | 6 | 8 | 7 | 7 | 7 | 7 |
| Perfume | 1 | 1 | 1 | 1 | 1 | 1 |
| Sodium Chloride | 0.5 | 1.0 | 0.3 | — | — | 0.5 |
| Stearyl Alcohol | — | — | — | 0.2 | 0.4 | 0.2 |
| Triclosan | 0.3 | 0.2 | 0.25 | 0.25 | 0.25 | 0.25 |
| Color Solution | 0.1 | 0.1 | 0.10 | 0.10 | 0.10 | 0.10 |

In maintaining the above six compositions, the compositions 1–3, which utilize the sodium chloride but not stearyl alcohol, remained clear up to nine months. The compositions 4 and 5, each of which included stearyl alcohol but no sodium chloride, remained clear for three to four months. On the other hand, the composition No. 6, having the combination of sodium chloride and stearyl alcohol, remained clear up to eighteen months. This shows the better results achieved using the combination of sodium chloride and stearyl alcohol, to provide a stick composition with improved clarity and appearance over a long period of time after formation of the composition.

While we have shown and described several embodiments in accordance with the present invention, it is understood that the same is not limited thereto, but is susceptible of numerous changes and modifications as known to those skilled in the art. Therefore, we do not wish to be limited to the details shown and described herein, but intend to cover all such changes and modifications as are encompassed by the scope of the appended claims.

We claim:

1. A solid clear cosmetic stick composition comprising (1) at least one material selected from the group consisting of polyhydric alcohol and monohydric alcohol, (2) water, and (3) alkali metal salts of saturated fatty acids as gelling agent for said at least one material and the water, and further including both sodium chloride and stearyl alcohol, the sodium chloride being included in the composition in an amount of at most 3.0% by weight, and the stearyl alcohol being included in the composition in an amount of at most 1.0% by weight, of the total weight of the composition, whereby crystal formation in the stick composition is reduced.

2. A solid clear cosmetic stick composition according to claim 1, wherein the composition further includes an active deodorant material, whereby the composition is a deodorant solid stick composition.

3. A solid clear cosmetic stick composition according to claim 1, wherein the alkali metal salts of saturated fatty acids are sodium salts of $C_{12}$–$C_{22}$ saturated fatty acids.

4. A solid clear cosmetic stick composition according to claim 1, wherein the stearyl alcohol is included in the composition in an amount of 0.1 to 1.0% by weight.

5. A solid clear cosmetic stick composition according to claim 1, wherein the at least one material is included in the composition in an amount of 50%–80% by weight, water is included in the composition in an amount of 15%–40% by weight, and the alkali metal salts of saturated fatty acids are included in the composition in an amount of 6%–9% by weight, of the total weight of the composition.

6. A solid clear cosmetic stick composition according to claim 1, wherein the sodium chloride is included in the composition in an amount of 0.1–3.0% by weight, and stearyl alcohol is included in the composition in an amount of 0.1–1.0% by weight.

7. A solid clear cosmetic stick composition according to claim 6, wherein the sodium chloride is included in the composition in an amount, by weight, of 0.3–0.6%, and stearyl alcohol is included in the composition in an amount, by weight, of 0.1–0.4%.

8. A solid clear cosmetic stick composition according to claim 6, wherein the at least one material is included in the composition in an amount of 50%–80% by weight, water is included in the composition in an amount of 15%–40% by weight, and the alkali metal salts of saturated fatty acids are included in the composition in an amount of 6%–9% by weight, of the total weight of the composition.

9. A solid clear cosmetic stick composition according to claim 1, wherein a saturated fatty acid distribution of the sodium salts of $C_{12}$–$C_{22}$ saturated fatty acids includes, by weight, 0–1% lauric acid, 4–10% myristic acid, 20–30% palmitic acid, 25–42% stearic acid, 15–18% arachidic acid and 17–20% behenic acid.

10. A solid clear stick composition according to claim 9, wherein the sodium chloride is included in the composition in an amount of 0.1–3.0% by weight, and stearyl alcohol is included in the composition in an amount of 0.1–1.0% by weight.

11. A solid clear cosmetic stick composition according to claim 10, wherein the composition further includes an active deodorant material, whereby the composition is a deodorant solid stick composition.

12. A solid clear cosmetic stick composition according to claim 11, wherein the composition includes, as the active deodorant material, perfume and a bacteriostat.

13. A solid clear cosmetic stick composition according to claim 10, wherein the at least one material includes propylene glycol.

14. A solid clear cosmetic stick composition according to claim 13, wherein the composition includes 50–80% by weight propylene glycol, 15–40% by weight water, and 6–9% by weight of the sodium salt of $C_{12}$–$C_{22}$ saturated fatty acids.

15. A solid clear cosmetic stick composition according to claim 14, wherein the composition further includes an active deodorant material, whereby the composition is a deodorant solid stick composition.

16. A solid clear cosmetic stick composition comprising (1) at least one material selected from the group consisting of polyhydric alcohol and monohydric alcohol, (2) water, and (3) alkali metal salts of saturated fatty acids as gelling agent for the at least one material and the water, and further including both sodium chloride and stearyl alcohol so as to reduce crystal formation in the stick composition as compared to crystal formation in a stick composition containing (1) said at least one material, (2) water, and (3) said alkali metal salts of saturated fatty acids as gelling agent, but not containing both sodium chloride and stearyl alcohol, the sodium chloride being included in the composition in an amount of at most 3.0% by weight, and the stearyl alcohol being included in the composition in an amount of at most 1.0% by weight, of the total weight of the composition.

17. A solid clear cosmetic stick composition according to claim 16, wherein said monohydric alcohol is ethanol.

18. A solid clear cosmetic stick composition according to claim 16, wherein the stearyl alcohol is included in the composition in an amount of 0.1 to 1.0% by weight.

19. A solid clear cosmetic stick composition according to claim 16, wherein the at least one material is included in the composition in an amount of 50%–80% by weight, water is included in the composition in an amount of 15%–40% by weight, and the alkali metal salts of saturated fatty acids are included in the composition in an amount of 6%–9% by weight, of the total weight of the composition.

20. A solid clear cosmetic stick composition according to claim 16, where the at least one material includes polyhydric alcohol.

21. A solid clear cosmetic stick composition according to claim 20, wherein the polyhydric alcohol is selected from the group consisting of propylene glycol, dipropylene glycol, glycerol, and sorbitol.

22. A solid clear cosmetic stick composition according to claim 16, wherein the sodium chloride is included in the composition in an amount of 0.1–3.0% by weight, and stearyl alcohol is included in the composition in an amount of 0.1–1.0% by weight.

23. A solid clear cosmetic stick composition according to claim 22, wherein the at least one material is included in the composition in an amount of 50%–80% by weight, water is included in the composition in an amount of 15%–40% by weight, and the alkali metal salts of saturated fatty acids are included in the composition in an amount of 6%–9% by weight, of the total weight of the composition.

24. A solid clear cosmetic stick composition according to claim 16, wherein the alkali metal salts of saturated fatty acids are sodium salt of saturated fatty acids.

25. A solid clear cosmetic stick composition according to claim 24, wherein the sodium salts of saturated fatty acids is sodium salts of $C_{12}$–$C_{22}$ saturated fatty acids.

26. A solid clear cosmetic stick composition according to claim 25, wherein the sodium chloride is included in the composition in an amount of 0.1–3.0% by weight, and stearyl alcohol is included in the composition is an amount of 0.1–1.0% by weight.

27. A solid clear cosmetic stick composition according to claim 16, wherein the alkali metal salts of saturated fatty acids are alkali metal salts of $C_{12}$–$C_{22}$ saturated fatty acids.

28. A solid clear cosmetic stick composition according to claim 27, wherein the alkali metal salts of $C_{12}$–$C_{22}$ saturated fatty acids are sodium salts of $C_{12}$–$C_{22}$ saturated fatty acids.

29. A solid clear cosmetic stick composition according to claim 28, wherein the sodium chloride is included in the composition in an amount of 0.1–3.0% by weight, and stearyl alcohol is included in the composition in an amount of 0.1–1.0% by weight.

* * * * *